US00PP27958P3

(12) United States Plant Patent
Perrault et al.

(10) Patent No.: US PP27,958 P3
(45) Date of Patent: May 2, 2017

(54) HOP PLANT NAMED 'ADHA 881'

(50) Latin Name: *Humulus lupulus*
Varietal Denomination: ADHA 881

(71) Applicants: Jason Perrault, Toppenish, WA (US); Eugene G. Probasco, Yakima, WA (US)

(72) Inventors: Jason Perrault, Toppenish, WA (US); Eugene G. Probasco, Yakima, WA (US)

(73) Assignee: AMERICAN DWARF HOP ASSOCIATION, LLC, Moxee, WA (US)

( * ) Notice: Subject to any disclaimer, the term of this patent is extended or adjusted under 35 U.S.C. 154(b) by 0 days.

(21) Appl. No.: 14/121,503

(22) Filed: Sep. 12, 2014

(65) Prior Publication Data

US 2015/0135381 P1 May 14, 2015

Related U.S. Application Data

(60) Provisional application No. 61/960,261, filed on Sep. 13, 2013.

(51) Int. Cl.
*A01H 5/02* (2006.01)

(52) U.S. Cl.
USPC ..... Plt./236

(58) Field of Classification Search
USPC ..... Plt./236
See application file for complete search history.

(56) References Cited

U.S. PATENT DOCUMENTS

PP23,674 P2 * 6/2013 Jeske et al. ..... Plt./236

* cited by examiner

*Primary Examiner* — Susan McCormick Ewoldt
(74) *Attorney, Agent, or Firm* — Ballew Law

(57) ABSTRACT

A new hop plant named 'ADHA 881' is disclosed. The cones of 'ADHA 881' mature in mid to late September in Moxee, Wash., and yield a crop of 2300 to 2400 pounds per acre. 'ADHA 881' is used for its aromatic quality.

4 Drawing Sheets

Genus and species: *Humulus lupulus*.
Variety denomination: 'ADHA 881'.

STATEMENT REGARDING FEDERALLY SPONSORED RESEARCH OR DEVELOPMENT

None

BACKGROUND OF THE INVENTION

'ADHA 881' is a product of a controlled breeding program carried out by the inventor in the Yakima Valley of Washington State. 'ADHA 881' was one of several seedlings resulting from cross number 08-067 made in 2008 with female parent 'Summit' (U.S. Plant Pat. No. 18,039) and male parent 'ADHA 75-2'. A single plant of 'ADHA 881' was selected in 2009.

In 2009 that single plant was asexually propagated in Toppenish, Wash. by softwood cuttings into 100 plants, which were planted in the area of Toppenish, Wash. These 100 plants were observed and evaluated for several years, and in 2011 were asexually propagated by softwood cuttings in Toppenish, Wash. into approximately 450 plants which were then planted in Moxee, Wash. for further observation and evaluation. In 2012, the 'ADHA 881' plants were again expanded by softwood cuttings in Toppenish, Wash. which were then planted in Moxee, Wash. for observation and evaluation of a large scale test plot. Throughout several generations of asexual propagation, 'ADHA 881' has been observed to retain its distinctive characteristics and has remained true to type.

BRIEF DESCRIPTION OF THE PHOTOGRAPHS

FIG. 3 illustrates the bine of a mature 'ADHA 881' hop plant; and.

Figure 1:
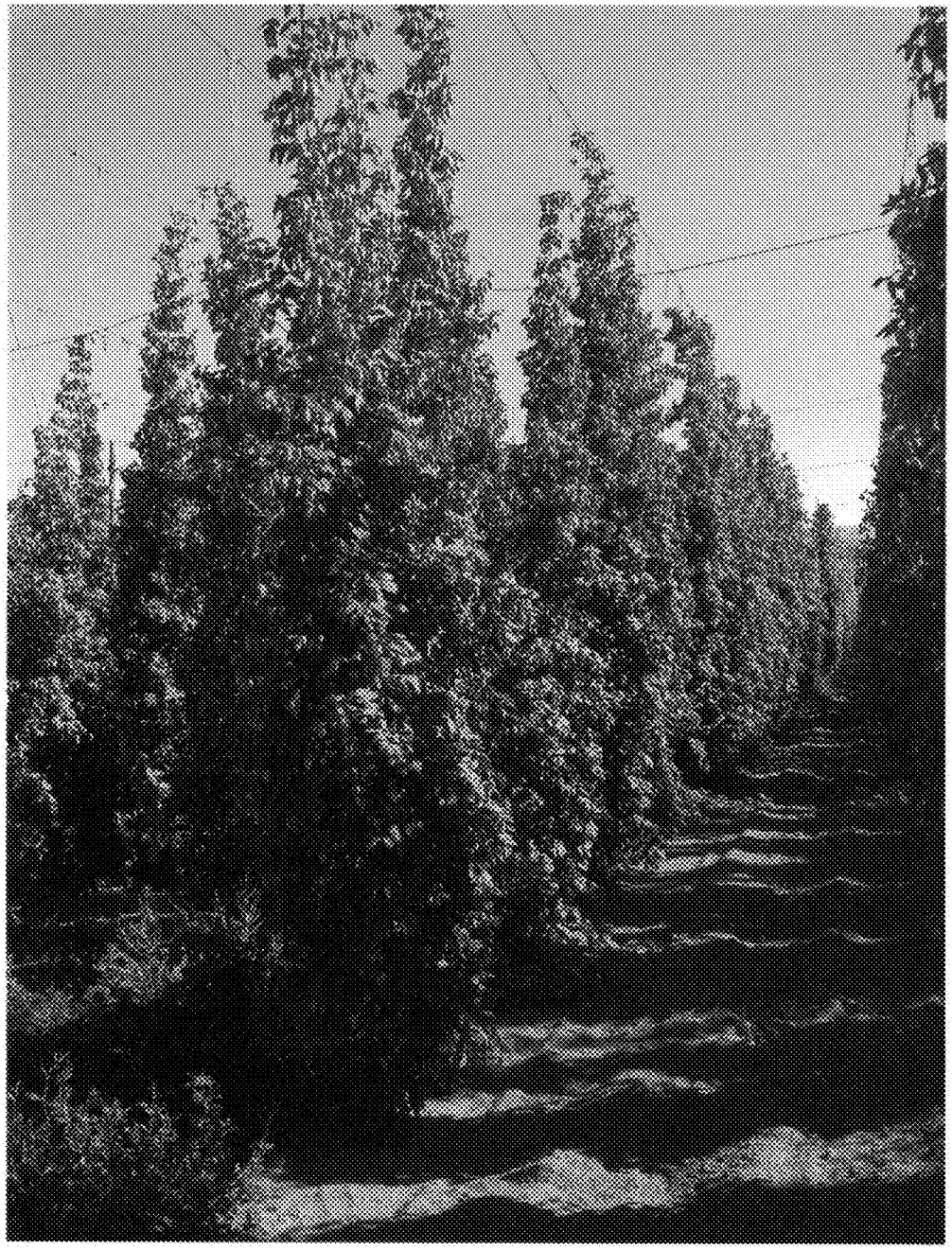
FIG. 1 illustrates a mature 'ADHA 881' hop plant grown on a trellis.
Figure 2:
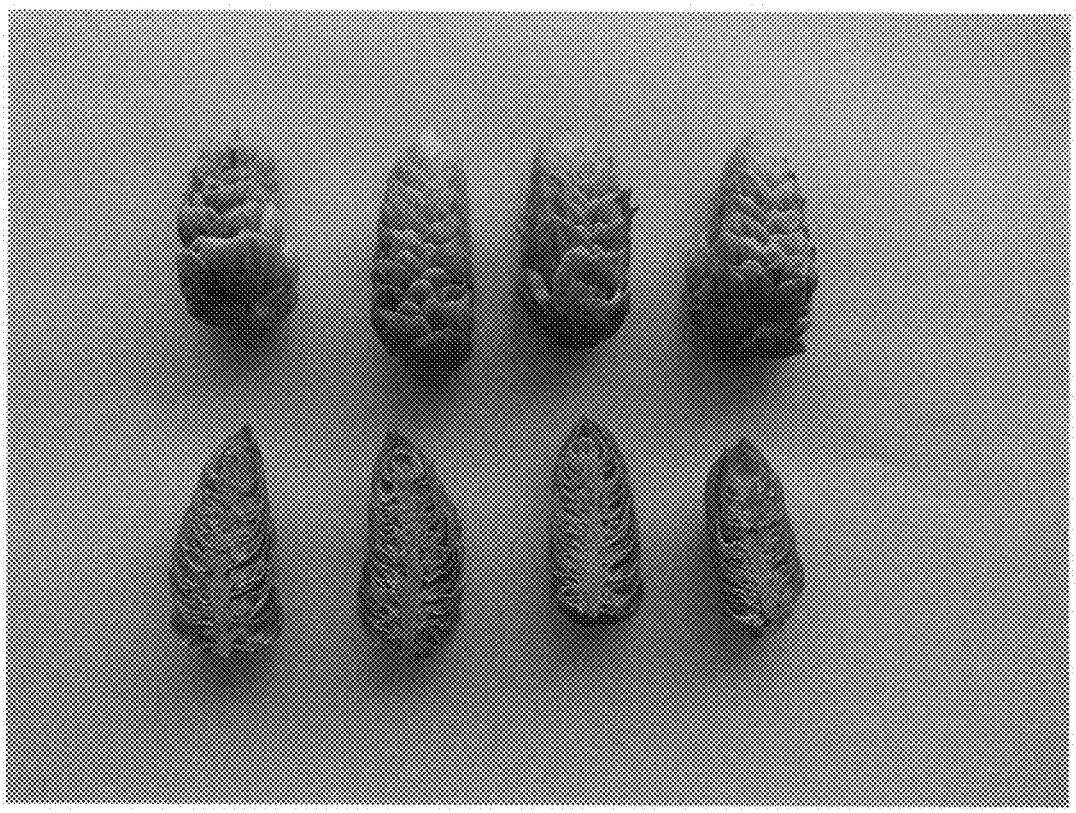
FIG. 2 illustrates whole cones and cross sections of cones of the 'ADHA 881' hop plant.
Figure 3:
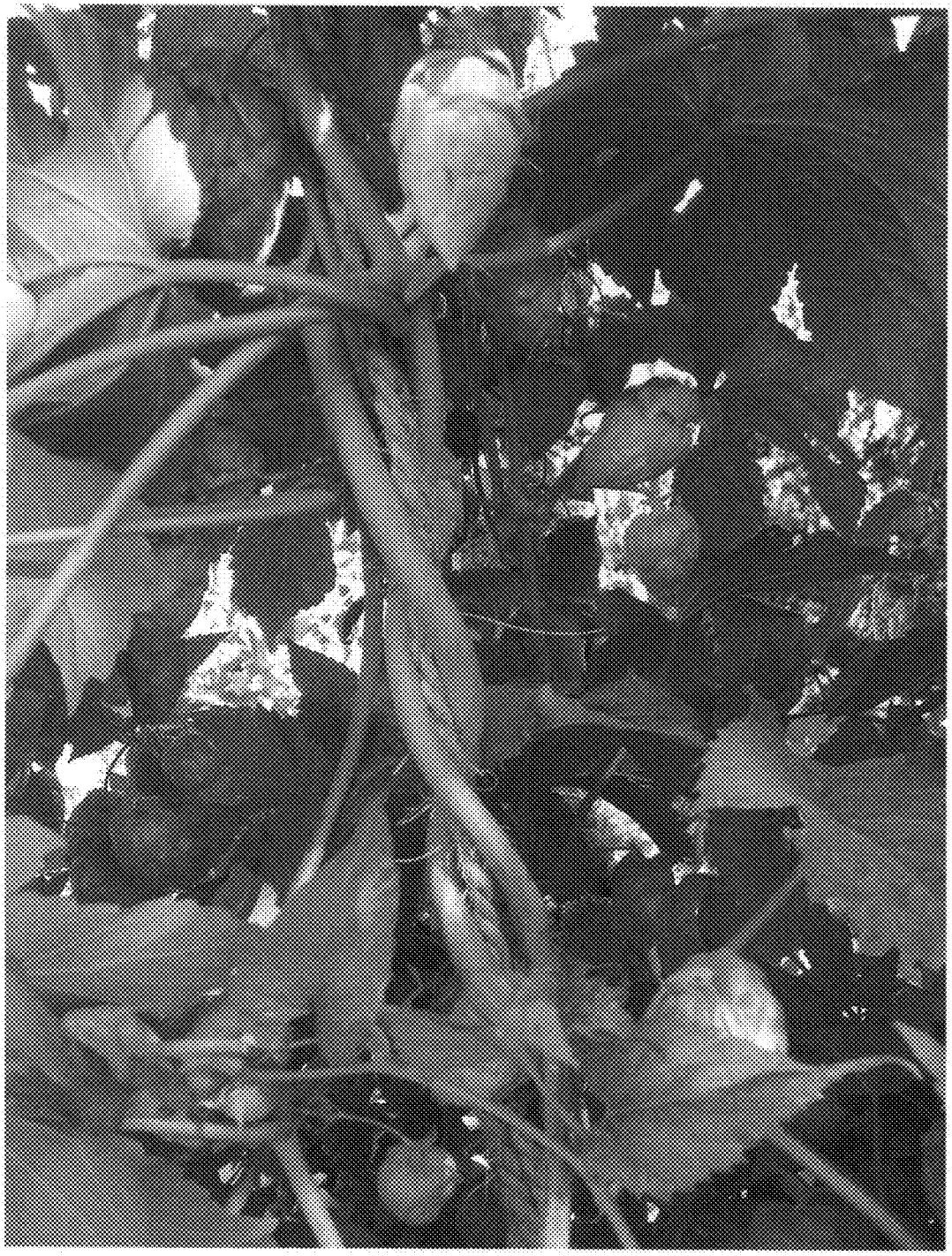
Figure 4:
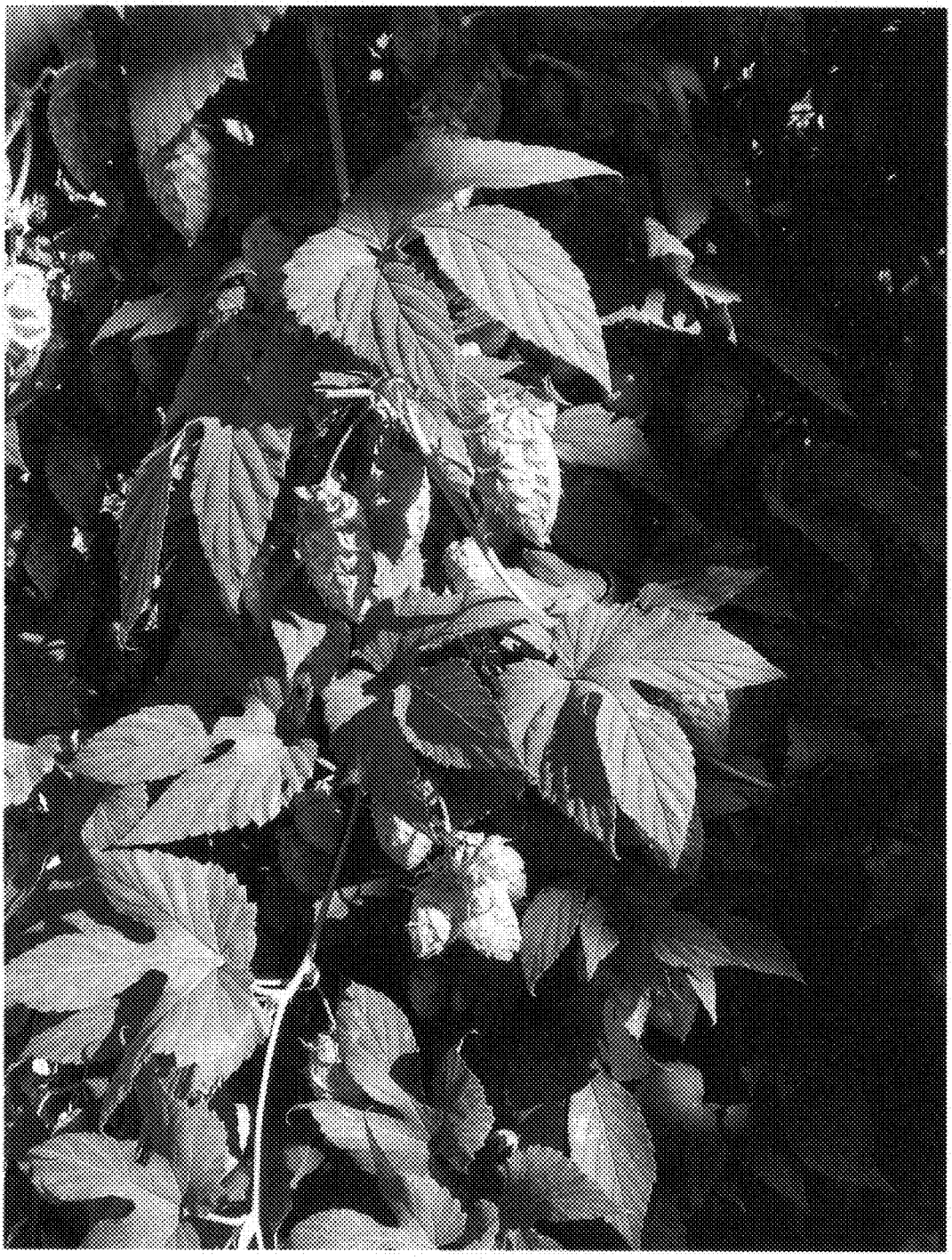
FIG. 4 illustrates the cones and leaves of a mature 'ADHA 881' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013 growing season at Moxee, Wash.

'ADHA 881' is distinguishable from its parent plants ('Summit' mother (U.S. Plant Pat. No. 18,039) and unpatented male parent 'ADHA 75-2'). 'ADHA 881' is distinguishable from its male parent 'ADHA 75-2' because ADHA 881 is a female plant with flowers that develop into mature hop cones without producing pollen, while flowers of 'ADHA 75-2', its male parent, will always produce pollen without developing into mature hop cones.

Table 1. sets forth some of the distinguishing characteristics of 'ADHA 881' as compared to its female parent 'Summit' and to the hop variety 'Toyomidori':

TABLE 1

| Characteristic | 'Toyomidori' | 'ADHA 881' | 'Summit' |
|---|---|---|---|
| Alpha Acid (α-Acids, % db) | 12.2 ± 0.6 | 15-17 | 18-19 |
| Beta Acids (β-Fraction, % db) | 7.2 ± 0.3 | 6.0-7.5 | 3.3-4.3 |
| Total Oil (ml/100 g) | 0.69 ± 0.19 | 3.6-4.3 | 1.5 |
| Myrcene (% of Total Oil) | 27 ± 5 | 40-55 | 48.5 |

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color chart used was The Royal Horticultural Society Colour Chart, Copyright 2001, and all color observations were made outdoors in full sunlight.

Ploidy: Diploid

Use: Brewing beer.

Harvest date: September 15 to 25 during the 2009-2012 growing seasons, Moxee, Wash.

Time of flowering: Considered to be early compared to other common hop varieties grown in Central Washington.

Crop yield: 2300 to 2400 pounds per acre.

Disease susceptibility: Tolerant of both downy mildew and powdery mildew.

Pest susceptibility: Average susceptibility to pests, including hop aphids and two spotted spider mites.

Plant shape: Columnar when grown on a typical hop trellis.

Bine:

*Color*.—Yellow Green Group 144B.

*Stripe*.—Not Present.

*Bine diameter*.—10.0 mm at base; 9.0 mm at 9 feet; and no measurement taken at terminal end.

*Stipule direction*.—Outward forked.

*Stipule color*.—Green Group 145A.

Leaf:

*Leaf arrangement*.—Opposite.

*Mature leaf shape*.—Palmately Lobed.

*Leaf apex shape*.—Apiculate with a dendate margin.

*Leaf base shape*.—Cordate.

*Color of mature leaf upper surface*.—Green Group 139A.

*Color of mature leaf lower surface*.—Yellow Green Group 147B.

*Average length of mature leaf*.—12 cm.

*Average width of mature leaf*.—18 cm.

*Number of lobes*.—5-7.

*Margin*.—Serrate.

*Serrations per inch*.—5-7.

*Vein color*.—Yellow Green Group 146C.

*Venation pattern*.—Palmate.

Petiole:

*Average petiole length (mature)*.—6.5 cm.

*Petiole average diameter*.—4.5 mm.

*Petiole color at base*.—Yellow Green Group 146B.

Cone:

*Cone shape*.—Ovate.

*Cone tip shape*.—Elliptic.

*Cone average length*.—3 cm.

*Cone average width*.—1.6 cm.

*Cone average weight*.—1.038 mg.

*Lupulin gland color*.—Ranging between Golden Yellow 2A to Yellow Green 150A (not distinctive of this variety).

*Lupulin gland shape*.—Pedunculated oblong polyps.

*Average number of lupulin glands per cone*.—63,360.

Bracts:

*Bract tip shape*.—Cuspidate alternating with rounded.

*Bract average length*.—1.5 cm.

*Bract average width*.—1.0 cm.

*Bract apex length*.—Medium.

*Bract tip position*.—Loosely appressed with cuspidate tips slightly flared.

*Bract tip color*.—Yellow Green Group 146A.

*Bract middle color*.—Yellow Green 139D.

*Bract base color*.—Yellow Green Group 145C.

*Average number of lupulin glands per bract*.—792.

Bracteoles:

*Bracteole color*.—Yellow Green Group 146A.

*Bracteole average length*.—1.0 cm.

*Bracteole average width*.—0.8 cm.

*Bracteole shape*.—Elliptic.

*Bracteole compactness*.—Closed.

Analytical characteristics:

*Alpha acid*.—15-17%.

*Beta acid*.—6.0-7.5%.

*Cohumulone*.—34-37%.

*Humulene*.—15-18% of total oils.

*Caryophyllene*.—8-11% of total oils.

*Myrcene*.—40-55% of total oils.

*Farnesene*.—<1% of total oils.

*Total oil*.—3.6-4.3 ml/100 g.

*Hop storage index (HSI)*.—The cones of the present variety experience a 26.9% transformation of alpha acids after about 6 months of storage at 22° C.

What is claimed is:

1. A new and distinct hop plant as shown and described herein.

* * * * *